(12) United States Patent
Broccatelli

(10) Patent No.: US 6,670,503 B2
(45) Date of Patent: Dec. 30, 2003

(54) METHOD FOR RECOVERY OF TEREPHTHALIC ACID FROM A MATERIAL CONTAINING POLY(ETHYLENE TEREPHTHALATES)

(76) Inventor: Massimo Broccatelli, Via Petrarca 6, 06083 Bastia Umbra (Peruglia) (IT)

( * ) Notice: Subject to any disclaimer, the term of this patent is extended or adjusted under 35 U.S.C. 154(b) by 0 days.

(21) Appl. No.: 09/792,567

(22) Filed: Feb. 21, 2001

(65) Prior Publication Data

US 2001/0023303 A1 Sep. 20, 2001

(30) Foreign Application Priority Data

Feb. 29, 2000 (EP) .............................................. 00830145

(51) Int. Cl.[7] .......................... C07C 51/09; C07C 63/14; C07C 51/42
(52) U.S. Cl. ....................... 562/483; 562/480; 562/485; 562/486; 562/487
(58) Field of Search ................................ 562/480, 483, 562/485, 486, 487

(56) References Cited

U.S. PATENT DOCUMENTS 5,254,666 A * 10/1993 Benzaria
5,430,174 A * 7/1995 Shono et al.
5,545,746 A   8/1996 Benzaria et al.

FOREIGN PATENT DOCUMENTS

| DE | 195 34 276 | 3/1997 |
| DE | 196 29 042 | 1/1998 |
| FR | 0 597 751 | 5/1994 |
| WO | PCT/AU95/00201 | 10/1995 |
| WO | WO/99/28285 | 6/1999 |

OTHER PUBLICATIONS wo 98/03459 European Search Report.

* cited by examiner

*Primary Examiner*—Johann Richter
*Assistant Examiner*—Paul A. Zucker
(74) *Attorney, Agent, or Firm*—James B. Conte; Barnes & Thornburg

(57) ABSTRACT

The present invention relates to a method of recovering terephthalic acid from a material containing poly(ethylene terephthalate) (P.E.T.) in the form of bottles, by making said material react, in the absence of water, with a reagent consisting of one or more metal salts of a weaker acid than the terephthalic acid, until a water-soluble compound is obtained, and subsequently carrying out dissolution in water and acidification.

18 Claims, No Drawings

METHOD FOR RECOVERY OF TEREPHTHALIC ACID FROM A MATERIAL CONTAINING POLY(ETHYLENE TEREPHTHALATES)

FIELD AND BACKGROUND OF THE INVENTION

The present invention relates to a method of recovering terephthalic acid from a material containing poly(ethylene terephthalate). In particular, the present invention relates to a method of obtaining terephthalic acid starting from poly (ethylene terephthalate (P.E.T.) materials, for instance in the form of bottles or other manufactured articles coming from a differentiated salvage dump.

Known in the art is the existence of some chemical methods involving recovery of terephthalic acid starting from materials containing poly(ethylene terephthalate).

Poly(ethylene terephthalate) (P.E.T.) is a saturated polyester resin made from terephthalic acid and ethylene glycol. P.E.T. is widely used in the food-industry packaging sector and in particular in the manufacture of bottles for soft drinks. Due to its large use, an increasingly growing interest in P.E.T. recycling has been developed in the most recent years.

Substantially chemical methods for terephthalic acid recovery are distinguishable from each other due to the mechanism used which can belong to one of the following main categories: alcoholysis, glycolysis, acid hydrolysis, neutral hydrolysis and alkaline hydrolysis.

Obviously, each individual mechanism can find application through various techniques differing from each other due, for example, to a different number of phases, different temperatures, pressures, involved reagents, reaction solvents.

The chemical method utilizing alcoholysis brings to formation of di(alkyl)-terephthalates, whereas glycolysis produces di(hydroxy-alkyl)-terephtalates.

Due to difficulties connected with purging of the obtained reaction products, these methods can only apply to materials containing poly(ethylene terephthalate) (P.E.T.) of high purity. Consequently these methods cannot apply if P.E.T. comes from a material obtained through a differentiated salvage dump as in the case of P.E.T. bottles from said differentiated dump.

The chemical method utilizing acid hydrolysis is carried out by making the P.E.T. react with a large excess of strong acid in solution, concentrated sulfuric acid for example. The sulfuric acid acts in a very short period of time, say some minutes, at a temperature included between room temperature and 95° C., by dissolving the starting P.E.T. with formation of terephthalic acid (TPA). The chemical method utilizing acid hydrolysis is scarcely applied in the industrial field, mainly due to the high corrosiveness of the reaction system and also due to the huge amount of salt solution produced for neutralizing the employed acid.

The chemical method utilizing neutral hydrolysis is conducted by treating the P.E.T. with water or steam, under pressure at a temperature included between 200 and 300° C., in the presence of appropriate catalysts. This method too has some drawbacks. The main disadvantages of this technology are represented by high energy consumptions and the impossibility of eliminating all mechanical impurities from the terephthalic acid (TPA) obtained by precipitation, such as undissolved particulate matter and insoluble polymers originally present in the starting material.

Finally, the chemical method utilizing alkaline hydrolysis is almost always carried out by use of alkaline hydroxides or ammonium hydroxides.

Use of these bases leads to formation of aqueous solutions of the corresponding salt of the terephthalic acid (TPA). These solutions can be easily cleared from mechanical impurities by filtering, flocculating or settling processes. In addition, terephthalic acid (TPA) is recovered from said aqueous solutions by precipitation in an acid medium.

Of all the above mentioned methods, the method utilizing alkaline hydrolysis has recently found many applications. Some of them are reproduced hereinafter:

a first application contemplates treatment of the P.E.T. with a concentrated solution of an alkaline hydroxide, under pressure and at temperatures close to or higher than 250° C. The P.E.T./alkaline solution ratio is greater than 20.

a second application contemplates treatment of the P.E.T. with a stoichiometric amount of an alkaline hydroxide in ethylene glycol (EG) at a temperature included between 100 and 200° C. If an ammonium hydroxide is used as the base, the method is carried out under pressure. In both cases, at all events, the obtained reaction mixture is dissolved in water.

Finally, a third application provides for the P.E.T. to be extruded in the presence of hydroxide at temperatures higher than 250° C. Subsequently, the obtained salt is dissolved in an aqueous solution.

Generally problems resulting from use of alkaline or alkaline-earth hydroxides or from use of concentrated solutions of such hydroxides are well known. For alkaline hydroxides it is meant a sodium hydroxide for example, for alkaline-earth hydroxide it is for example meant a calcium hydroxide.

The main disadvantages are connected with difficulties in manipulating these types of very aggressive reagents by operators. In addition, modifications in the plants are required to be adopted together with a series of technical expedients in plant construction due to the big problems connected with corrosion of these reagents, above all if used in solution.

In the above first application, disadvantages consist in being obliged to heat, filter and recover great amounts of solution. In addition, in this application use of great amounts of hydroxides and adoption of high pressures is provided.

In the above second and third applications, the main disadvantage resides in the fact that it is impossible to obtain terephthalic acid (TPA) free from undesirable yellow-pink colorations. In fact, in the absence of water the hydroxides employed at temperatures higher than 100° C. react with the ethylene glycol (EG) resulting from the hydrolysis reaction. The reaction between hydroxides and ethylene glycol brings to formation of strongly red-colored and water-soluble products. Formation of these colored compounds prevents precipitation of uncontaminated white TPA. Therefore, the terephthalic acid (TPA) containing colored impurities must be bleached.

Methods described in literature for TPA bleaching are long and expensive. Some methods of bleaching for example involve extraction of impurities by use of water-insoluble higher alcohols.

In addition, the above third application requires use of starting material containing P.E.T. in the form of ground, washed and dried scraps, which will involve an increase in the costs of the starting raw material.

Therefore there is a need for a method of recovering terephthalic acid from a material containing polyethylene terephthalate), coming for example from a differentiated salvage dump, which is devoid of the drawbacks of the known art.

In particular, a method is required which enables recovery of a terephthalic acid free from colored contaminations and impurities.

Still more particularly, there is a need for a method of recovering terephthalic acid which does not involve use of alkaline hydroxides, alkaline-earth hydroxides and ammonium hydroxide or concentrated solutions of these hydroxides.

In addition, there is a requirement for a method of recovering terephthalic acid which is particularly cheap. This is very important when a raw material of low value is to be treated, such as the material from a differentiated salvage dump for example. For the above reasons, the volumes of the materials to be heated must be reduced, if possible. In addition, secondary reactions producing by-products must be reduced or eliminated, such as the above mentioned colored contaminations.

Finally, also useful is a reduction in the amount of solvent or water used for the purpose of reducing the amounts of strong acids to employ for acidification of the solution of the metal salt or salts of the TPA so as to obtain precipitation thereof. In addition, a limited use of solvent and water amounts enables the cost of the individual processes to be controlled.

SUMMARY OF THE INVENTION

It is an aim of the present invention to provide a method of recovering terephthalic acid devoid of colored contaminations starting from a material containing poly(ethylene terephthalate).

Another aim of the invention is to provide a method of recovering terephthalic acid that does not use alkaline hydroxides, alkaline-earth hydroxides and ammonium hydroxide or concentrated solutions of these hydroxides.

It is a further aim of the invention to provide a method of recovering terephthalic acid in which a starting reagent-heating step is not required.

The foregoing and still further objects that will also become more apparent during the following detailed description have been achieved by the Applicant that has surprisingly found out that recovery of terephthalic acid from materials containing poly(ethylene terephthalate) is possible and advantageous, for example in the case of waste materials in the form of bottles or other manufactured articles coming from a differentiated salvage dump, by making said materials react in the absence of water, with a reagent consisting of one or more metal salts of weaker acids than the terephthalic acid, until a water-soluble reaction compound is obtained which comprises soluble chemical species containing chemically-bound TPA and possible parts of unreacted P.E.T. or parts of material of different nature from P.E.T. which are present in the waste material.

Therefore it is an object of the present invention to provide a method of recovering terephthalic acid (TPA) from materials containing poly(ethylene terephthalate) (P.E.T.) through precipitation by acidification with a stronger acid than TPA of an aqueous solution comprising one or more water-soluble metal salts of the TPA and subsequent separation, washing and drying of the precipitated TPA, wherein said solution comprising one or more metal salts of the TPA is obtained by a process comprising the following steps:

a) mixing, in the absence of water, a reaction mixture comprising said material containing P.E.T. and one or more water-soluble salts of weaker acids than the TPA until a water-soluble reaction compound is obtained; said soluble compound being comprised of soluble chemical species obtained following interaction between P.E.T. and said metal salts of weaker acids than the TPA and possible parts of the unreacted P.E.T. or parts of material of different nature than P.E.T., present in the starting material;

b) adding a fraction of water to the soluble compound obtained from step a), until a reaction of salifying the TPA contained in said soluble chemical species is carried out, so that an aqueous solution is obtained which comprises one or more metal salts of the TPA, ethylene glycol and possible parts of the unreacted starting material.

It is a further object of the present invention to provide a method of recovering terephthalic acid as above described, wherein said solution comprising one or more metal salts of the TPA is obtained by a process comprising the following steps:

a) mixing, in the absence of water, a reaction mixture comprising said material containing P.E.T. and one or more metal salts of weaker acids than the TPA until a water-soluble reaction compound is obtained; said soluble compound being comprised of soluble chemical species obtained following interaction between the P.E.T. and said metal salts of weaker acids than the TPA and possible parts of unreacted P.E.T. or parts of material of different nature than the P.E.T., present in the starting material;

b) adding a first portion of water to the obtained soluble compound, until a reaction of salifying the TPA contained in said soluble chemical species is achieved but not the complete dissolution of said species, a semi-solid paste being obtained;

c) eliminating the volatile components present in the semi-solid paste of step b) to obtain a solid residue;

d) adding a second portion of water to the solid residue obtained from step c), until the TPA is completely solubilized and an aqueous solution comprising one or more metal salts of the TPA is obtained.

Further technical features and the advantages of the present invention will be best understood from the following detailed description.

Some preferred embodiments of the present invention are described in appended dependent claims.

In accordance with the present invention, the starting material containing poly(ethylene terephthalate) (P.E.T.), for instance waste material in the form of unbroken bottles or small fragments, fibers, ground scraps or films, is set in a mixer device.

The mixer device can be of mechanical or electrical operation. Preferably, in a preferred embodiment it can be a reactor equipped with a stirrer or, alternatively, it can be a propeller reactor, the propeller being anchored to the device bottom. The propeller preferably rotates at a speed adapted to enable grinding of the starting material and cause heating by friction of same. The mixing speed is preferably included between 300 and 1600 revolutions per minute rpm; more preferably between 600 and 1600 rpm. Advantageous results have been reached at a speed included between 800 and 1500 rpm; more preferably between 900 and 1450 rpm.

Added to the starting material is a reagent in a solid form, so that the whole forms a reaction mixture in the absence of water. Alternatively, the reagent can be added after a mechanical pre-treating step of the starting material.

The reagent used is made up of an anhydrous composition comprising one or more metal salts of weaker acids than the terephthalic acid. These metal salts must have a metallic cation forming water-soluble salts with the TPA.

Practically, if the types of salts used are wished to be represented by a chemical formula, we can say that these salts are selected from a group consisting of salts having $M_n X_m$ (n=valence of anion X and m=valence of cation M) as the general chemical formula; wherein M=metal of valence m supplying water-soluble terephthalates such as for example sodium, potassium, zinc, antimony and tin; and X=cation of a weaker acid than the terephthalic acid.

The terephthalic acid has a pKa of 3.51. The dissociation constants pK1 and pK2 for the terephthalic acid at a temperature of 25° C. are 3.54 and 4.46, respectively.

As a reference parameter to establish the force of an acid, the value herein assumed is that of the dissociation constant of an acid in water, i.e. the value of Ka or Kb, knowing that $Kw = Ka \cdot Kb = 10^{-14}$.

For instance, the acids that can be used in salts $M_n X_m$ are selected from inorganic weak acids such as $H_2CO_3$, $H_2S$, $HNO_2$, $H_3BO_4$, $HClO$, $H_3BO_3$ or from aliphatic organic acids (with the exclusion of formic acid and the acids alpha-substituted with electron-attractor groups like halogens, —OH, —SH, —CHO, —CRO, —CN, —COOH) such as acetic acid, propionic acid, acrylic acid, or aromatic acids such as benzoic acid, meta or para-toluic acid and acids having groups like —OH, —OR and —NH₂ as substituent in the aromatic ring. Further possible examples of salts $M_n X_m$ finding application in the method of the present invention are represented by: carbonates, bicarbonates, borates (orthoborates, metaborates, perborates and tetraborates), acetates, benzoates and salicylates.

Preferably used are sodium carbonate, potassium carbonate, sodium bicarbonate, potassium bicarbonate, sodium sulfide, sodium acetate, potassium acetate, antimony triacetate, zinc acetate and sodium tetraborate.

Preferably, mixtures of the above salts are used; for instance, the following mixtures have been found very advantageous: 50% $Na_2CO_3$/50% $K_2CO_3$, 50% $(CH_3COO)_3Sb$/50% $CH_3COONa$, 50% $(CH_3COO)_3Sb$/50% $(CH_3COO)_2Zn$.

Preferably, the reaction mixture of the mixing step a) comprises an amount by weight of reagent capable of ensuring, at the end of the process of the invention, complete salification of all molecules of terephthalic acid. The terephthalic acid has two carboxyl groups to be salified. Theoretically, the reagent amount used is at least sufficient to salify one of the two carboxyl groups of the terephthalic acid present in the starting P.E.T. Consequently, the reagent used is capable of ensuring at least one metal equivalent per mole of terephthalic acid to be salified.

In practice, an excess of reagent is always used independently of the type of salt and the type of salt mixture employed. By way of example, the Applicant in texts carried out has taken into account the amounts of salts commonly used.

Preferably, the reaction mixture of the mixing step a) comprises an amount by weight of reagent capable of ensuring at least one monovalent metal equivalent per mole of terephthalic acid to be salified. More preferably, an amount by weight included between at least one equivalent and ten equivalents of monovalent metal per mole of terephthalic acid to be salified. Most preferably, an amount by weight included between one and four equivalents of monovalent metal per mole of terephthalic acid to be salified.

The reaction mixture is mixed under ambient pressure and in the absence of water until, by effect of a mechanical working, the reaction mixture is changed to a water-soluble reaction compound.

The reaction mixture is mixed over a period of time preferably included between 5 and 200 minutes; more preferably over a period of time included between 10 and 140 minutes; most preferably over a period of time included between 15 and 100 minutes.

Following the mechanical working, the temperature within the device reaches the desired value, at ambient pressure.

Alternatively, heating means such as electric resistors, circulation of heating fluids, induction heaters and microwave ovens can be used. Preferably, the heating means is used to bring the reaction mixture to the desired temperature or, alternatively, to keep temperature constant to a given value.

Preferably, the temperature is included between 90 and 260° C.; more preferably values included between 95 and 220° C. and most preferably values included between 100 and 190° C. are involved.

Heating of the reaction mixture at the above temperatures takes place by mechanical action due to mixing of the reaction mixture in the mixing device. Alternatively, heating is obtained by external heating means.

Surprisingly, the applicant has found that at the above temperatures the P.E.T. present in the reaction mixture changes to an intermediate product having the unexpected property of being highly water soluble. Said product comprises soluble chemical species containing unfree TPA in their structure. The soluble chemical species are obtained following an interaction between the P.E.T. and said metal salts of weaker acids than the terephthalic acid. Possibly, the water-soluble reaction compound, in addition to the chemical species, comprises portions of unreacted P.E.T. or part of material of different nature than P.E.T., present in the starting material. Practically, the poly(ethylene terephthalate) is submitted to a "digestion" step, under ambient pressure and in the absence of water, with the $M_n X_m$ salts used. The reaction compound containing the intermediate product physically has a consistency varying between that of a moist powder (if ethylene glycol has not been added) and that of a paste in a melted or semi-solid state (if ethylene glycol has been added). From a chemical point of view, it can be assumed that the poly(ethylene terephthalate) polymer, by interacting with the reagent, reduces its average molecular weight and the chains of smaller size that are formed have, at their terminations, carboxyl groups salified with the reagent metals and consequently are water-soluble.

Therefore, in accordance with the present invention, the water-insoluble starting material, following treatment with a solid reagent in the absence of water, is changed to a water-soluble intermediate product or compound because it contains smaller chains having salified carboxyl groups.

The soluble compound may also comprise the ethylene glycol possibly created following interaction with one or more metal salts of weaker acids than the terephthalic acid during the mechanical working. Alternatively, the soluble compound can also contain the ethylene glycol added in the mixing step.

Alternatively, the intermediate product may comprise a portion of starting material that did not react with the reagent.

The Applicant has surprisingly found that the ethylene glycol under these specific work conditions, does not react with the salts of formula $M_n X_m$ present in the reaction medium and consequently there is no formation of colored contaminations and impurities that would pollute the final terephthalic acid.

In addition, the Applicant has found that the ethylene glycol formed does not have to be removed from the reaction medium since its presence does not hinder recovery of the produced terephthalic acid.

In a preferred embodiment the Applicant has carried out adding of an amount of ethylene glycol to the reaction mixture. Preferably, the reaction mixture will be comprised of: the material containing poly(ethylene terephthalate) (P.E.T.) and ethylene glycol possibly added in a ratio by weight included between 10:1 and 1:10; preferably in a ratio by weight included between 7:1 and 1:7; more preferably the ratio by weight will be included between 4:1 and 1:4.

The ethylene glycol possibly added can be at room temperature or alternatively can be heated to a temperature included between 100 and 190° C.

The ethylene glycol that is possibly added aims at improving heat distribution within the mixer device as well as at improving (speeding up) interaction between the P.E.T. chains and the metal salts of weaker acids than the terephthalic acid.

Subsequently, the compound obtained from the intermediate mixing is brought into contact with a fraction of said aqueous medium until a reaction of complete hydrolysis of said soluble chemical species and salification of the TPA contained therein is achieved.

Preferably, the water portion is in a ratio by weight included between 4 and 30 parts of reaction mixture; more preferably it is included between 8 and 25 parts; most preferably it is included between 10 and 20 parts of the reaction mixture.

The intermediate product is held under stirring over a period of time included between 10 and 100 minutes; more preferably over a period of time included between 20 and 70 minutes.

Following addition of water to the soluble compound, a solution is obtained that comprises one or more metal salts of the TPA, ethylene glycol, unreacted parts of said metal salts, parts of water-soluble acids, weaker than the TPA liberated from said metal salts by reaction with the TPA and that did not move away from the reaction medium by evaporation, and possible parts of unreacted P.E.T. or parts of material of different nature than the P.E.T., present in the starting materials (the last mentioned parts being present in the solution as bottom body).

Possibly, the obtained solution can be heated to a temperature included between 20 and 100° C.; more preferably to a temperature included between 40 and 90° C.

Under these conditions, the soluble chemical species are divided into TPA molecules salified with the cations of the $M_nX_m$ salts and ethylene glycol.

Practically, said solution comprises ethylene glycol, terephthalic acid salified with a metal, water, $M_nX_m$ salt and impurities present in the starting material (P.E.T.), such as coloring substances, unsolubilized polymers, unreacted P.E.T., paper and others.

Subsequently, an amount of stronger acid than TPA is added to said first solution for the purpose of creating the appropriate conditions for causing precipitation of the terephthalic acid from said solution.

Preferably, said solution can be submitted to filtering and/or washing steps for the purpose of removing impurities present therein, before addition of the strong acid.

Practically, the salt of the terephthalic acid salified with a metal, contained in said solution, in the presence of the strong acid is changed to a water-insoluble terephthalic acid and the corresponding salt. For example $TPA(Na)_2 + H_2SO_4 \rightarrow TPA(H)_2 + 2Na^+ + SO_4^{2-}$.

Depending on the temperature conditions, ionic force and acidity of the obtained solution after treatment with a strong acid, said salt can precipitate or remain in solution.

As strong acids, the following can be preferably employed: $H_2SO_4$, HCl, $HNO_3$, $H_3PO_4$ and HCOOH.

The terephthalic acid precipitated in said solution is separated from the remaining liquid portion. The liquid portion will be comprised of: water, salt formed following acidification of said first solution, ethylene glycol formed from the full hydrolysis reaction and ethylene glycol possibly added, weaker acids that are formed and do not move away from the reaction medium by evaporation.

Preferably, the ethylene glycol present in the liquid portion can be recovered. For example, the ethylene glycol can be drawn out by distillation at ambient pressure or under vacuum.

It is a further object of the present invention a method of recovering terephthalic acid from a material containing P.E.T. in which, after obtaining the soluble compound, a first portion of water is added which is sufficient to carry out a full hydrolysis of said soluble chemical species and salification of the TPA contained therein, but not to carry out a full dissolution of the reaction compound, thereby obtaining a moist powder and/or a solid or semi-solid paste.

Preferably, an amount of water included between 0.1 and 3 parts of the obtained paste is used; more preferably 0.3 to 2 parts; most preferably 0.5 to 1 part.

Subsequently, in the same reaction medium where the semi-solid paste is present, the volatile components present in said semi-solid paste are moved away. The volatile components may for example comprise water, ethylene glycol formed during the mixing step or ethylene glycol added to the reaction mixture, or others. To eliminate the volatile components, common means known to those skilled in the art can be used. After the volatile components are eliminated, a solid residue is obtained which contains portions of salified TPA and partly unreacted P.E.T. and others. Subsequently, a second portion of water is added to the solid residue. Preferably an amount of water included between 4 and 30 parts of the obtained paste is employed; more preferably 8 to 25 parts; most preferably 10 to 20 parts, until complete solubilization is reached and an aqueous solution is obtained which comprises one or more metal salts of the TPA, ethylene glycol, unreacted material, water. This solution can then be submitted to filtering and/or washing steps and acidification with a stronger acid than the above TPA.

The method of the invention does not contemplate use of alkaline hydroxides such as caustic soda NaOH and ammonium hydroxide $NH_4OH$.

In addition, the steps provided by the method of the invention can be carried out both following a continuous modality and a batch modality, without any limitations as far as plants are concerned.

The yield of the method of the present invention can vary based on the operating conditions and will depend on some process variables.

The method of the present invention has all the advantages of the methods based on alkaline hydrolysis presently known in the art, without having any of the drawbacks connected therewith, such as for example:

necessity to operate with great volumes of solution and hydrolysis;

necessity to operate under pressure;

production of colored by-products that will cause pollution of the TPA produced;

necessity to eliminate the ethylene glycol being formed from the reaction medium; and necessity to operate with washed and dried P.E.T.

The method of the present invention also represents a method of separation of P.E.T. from other plastic materials. In fact in this method it is also possible to use scraps of P.E.T. containing even important amounts of plastic materials of different nature that, as they do not react and do come out of the reaction medium unaltered, can be easily separated by filtering from the solution containing the salt of a metal of the terephthalic acid.

One of the preferred embodiments of the present invention is now given hereinafter, by way of example. This embodiment must not be considered as a limitation of the present invention.

EXAMPLE

The examples below, 1–75, have been carried out in two different reactors.

Reactor No. 1 consists of a cylinder with a diameter of 1 m and a height of 1.5 m, to the bottom of which a propeller rotating at a fixed speed of 1420 r.p.m. is fastened. This reactor is equipped with heating resistors.

Reactor No. 2 consists of a cylinder with a diameter of 1 m and a height of 2.8 m, equipped with a propeller-stirrer having a speed varying between 300 and 600 r.p.m. and with heating resistors.

Examples 1 to 60 have been carried out in reactor No. 1 with the following modalities: the reactor is loaded with 50 kg of P.E.T. bottles, from a differentiated salvage dump, which still hold polypropylene (PP) caps and polyethylene (PB) or paper labels, so that P.E.T. content in the charge is about 90% of the total amount=45 kg. Loading is carried out while the propeller is rotating, at ambient pressure, in the absence of water and with the heating resistors turned off.

The loaded material is left under very strong stirring for about 10 minutes, so that bottles are ground and heated by friction to about 100° C.

At this point a reagent is added which comprises one or more salts of weaker acids than TPA or mixtures of same in the absence or in the presence of ethylene glycol, already heated to the desired reaction temperature (100–190° C.), and the heating resistors are switched on to maintain said temperature, and the reaction is allowed to go on until it comes to an end.

A convenient manner to follow the reaction course is based on measurement of the amounts of liberated weak acid; this is particularly simple where carbonates or acetates are concerned; in fact when evolution of $CO_2$ or of acetic acid ceases the reaction has come to an end.

When this step a) of the mixing process has been completed, water is added which, by evaporating, cools the reaction mixture to a temperature below 100° C. At this point further water is added and the mixture is maintained under stirring at a temperature included between 40 and 99° C. until complete dissolution of the soluble species present in the reaction mixture is reached. The solution is filtered and sent to the stage of acidification and precipitation of the TPA with a stronger acid than the terephthalic acid, such as $H_2SO_4$, HCl, $HNO_3$, $H_3PO_4$, HCOOH. Thus step b) has been carried out, the process yields are measured by putting the solid residue resulting from filtration into water, separating the supernatant portion (PP, PE, cellulose) from the bottom body (ground and unreacted PET), drying and weighing said bottom body. Practically the unreacted P.E.T. gives the yield value.

Examples 61 to 75 have been carried out in reactor No. 2.

In this reactor higher amounts of ethylene glycol are required to be used so that the reaction mixture may be conveniently stirred. In this case the reagents are simultaneously loaded and the reaction times are measured at the moment that the system reaches the desired reaction temperature by effect of heating exclusively due to the heating resistors (since in this case friction due to stirring produces negligible heat). Modalities are the same as in examples 1 to 60.

The results are reproduced in the Table below.

| Ex. No. | Salt or mixture of metal salts | kg of salt or mixture of metal salts | kg of ethylene glycol | Reaction temp. ° C. | Reaction time Minutes | Reacted PET % |
|---|---|---|---|---|---|---|
| 1 | $Na_2CO_3$ | 12,425 | 0 | 100 | 120 | 8 |
| 2 | $Na_2CO_3$ | 12,425 | 0 | 150 | 120 | 32 |
| 3 | $Na_2CO_3$ | 12,425 | 0 | 190 | 120 | 45 |
| 4 | $Na_2CO_3$ | 24,850 | 0 | 100 | 120 | 17 |
| 5 | $Na_2CO_3$ | 24,850 | 0 | 150 | 105 | 40 |
| 6 | $Na_2CO_3$ | 24,850 | 0 | 190 | 75 | 52 |
| 7 | $Na_2CO_3$ | 36,000 | 0 | 100 | 120 | 25 |
| 8 | $Na_2CO_3$ | 36,000 | 0 | 150 | 90 | 50 |
| 9 | $Na_2CO_3$ | 36,000 | 0 | 190 | 60 | 60 |
| 10 | $Na_2CO_3$ | 12,425 | 5 | 100 | 33 | 60 |
| 11 | $Na_2CO_3$ | 12,425 | 5 | 150 | 19 | 72 |
| 12 | $Na_2CO_3$ | 12,425 | 5 | 190 | 14 | 80 |
| 13 | $Na_2CO_3$ | 24,850 | 5 | 100 | 30 | 63 |
| 14 | $Na_2CO_3$ | 24,850 | 5 | 150 | 15 | 74 |
| 15 | $Na_2CO_3$ | 24,850 | 5 | 190 | 11 | 82 |
| 16 | $Na_2CO_3$ | 36,000 | 5 | 100 | 27 | 65 |
| 17 | $Na_2CO_3$ | 36,000 | 5 | 150 | 12 | 77 |
| 18 | $Na_2CO_3$ | 36,000 | 5 | 190 | 9 | 85 |
| 19 | $Na_2CO_3$ | 12,425 | 30 | 100 | 30 | 65 |
| 20 | $Na_2CO_3$ | 12,425 | 30 | 150 | 15 | 79 |
| 21 | $Na_2CO_3$ | 12,425 | 30 | 190 | 9 | 88 |
| 22 | $Na_2CO_3$ | 24,850 | 30 | 100 | 25 | 67 |
| 23 | $Na_2CO_3$ | 24,850 | 30 | 150 | 12 | 80 |
| 24 | $Na_2CO_3$ | 24,850 | 30 | 190 | 7 | 90 |
| 25 | $Na_2CO_3$ | 36,000 | 30 | 100 | 20 | 70 |
| 26 | $Na_2CO_3$ | 36,000 | 30 | 150 | 9 | 83 |
| 27 | $Na_2CO_3$ | 36,000 | 30 | 190 | 5 | 92 |
| 28 | $Na_2CO_3$ | 12,425 | 70 | 100 | 25 | 67 |
| 29 | $Na_2CO_3$ | 12,425 | 70 | 150 | 13 | 82 |
| 30 | $Na_2CO_3$ | 12,425 | 70 | 190 | 6 | 90 |
| 31 | $Na_2CO_3$ | 24,850 | 70 | 100 | 23 | 69 |
| 32 | $Na_2CO_3$ | 24,850 | 70 | 150 | 11 | 84 |
| 33 | $Na_2CO_3$ | 24,850 | 70 | 190 | 6 | 92 |
| 34 | $Na_2CO_3$ | 36,000 | 70 | 100 | 16 | 72 |
| 35 | $Na_2CO_3$ | 36,000 | 70 | 150 | 8 | 85 |
| 36 | $Na_2CO_3$ | 36,000 | 70 | 190 | 5 | 94 |
| 37 | $K_2CO_3$ | 16,200 | 0 | 100 | 120 | 7,5 |
| 38 | $K_2CO_3$ | 32,400 | 0 | 150 | 115 | 42 |
| 39 | $K_2CO_3$ | 48,500 | 0 | 190 | 60 | 60 |
| 40 | $K_2CO_3$ | 32,400 | 5 | 190 | 12 | 78 |
| 41 | $K_2CO_3$ | 32,400 | 30 | 190 | 8 | 88 |
| 42 | $K_2CO_3$ | 32,400 | 70 | 190 | 7 | 90 |
| 43 | $K_2CO_3$ | 48,500 | 70 | 190 | 69 | 92 |
| 44 | $Na_2CO_3$ | 39,400 | 0 | 190 | 80 | 55 |
| 45 | $Na_2CO_3$ | 39,400 | 5 | 190 | 110 | 78 |
| 46 | $Na_2CO_3$ | 39,400 | 30 | 190 | 7 | 88 |
| 47 | $Na_2CO_3$ | 39,400 | 70 | 190 | 6 | 90 |
| 48 | 50% $Na_2CO_3$ 50% $K_2CO_3$ | 28,650 | 0 | 190 | 75 | 50 |
| 49 | 50% $Na_2CO_3$ 50% $K_2CO_3$ | 28,650 | 5 | 190 | 10 | 80 |
| 50 | 50% $Na_2CO_3$ 50% $K_2CO_3$ | 28,650 | 30 | 190 | 8 | 90 |
| 51 | 50% $Na_2CO_3$ 50% $K_2CO_3$ | 28,650 | 70 | 190 | 7 | 91 |
| 52 | $Na_2S$ | 18,300 | 30 | 190 | 10 | 85 |
| 53 | $CH_3COONa$ | 19,300 | 30 | 190 | 15 | 80 |
| 54 | $CH_3COONa$ | 39,500 | 30 | 190 | 12 | 85 |
| 55 | $(CH_3COO)_3Sb$ | 46,500 | 5 | 190 | 14 | 89 |

-continued

| Ex. No. | Salt or mixture of metal salts | kg of salt or mixture of metal salts | kg of ethylene glycol | Reaction temp. ° C. | Reaction time Minutes | Reacted PET % |
|---|---|---|---|---|---|---|
| 56 | $(CH_3COO)_3Sb$ | 46,500 | 30 | 190 | 9 | 91 |
| 57 | 50% $(CH_3COO)_3Sb$ 50% $CH_3COONa$ | 37,000 | 5 | 190 | 12 | 88 |
| 59 | 50% $(CH_3COO)_3Sb$ 50% $(CH_3COO)_2Zn$ | 66,000 | 30 | 190 | 8 | 94 |
| 60 | $(CH_3COO)_2Zn$ | 43,000 | 30 | 190 | 9 | 95 |
| 61 | $Na_2CO_3$ | 12,425 | 150 | 100 | 35 | 85 |
| 62 | $Na_2CO_3$ | 24,850 | 150 | 150 | 15 | 90 |
| 63 | $Na_2CO_3$ | 36,000 | 150 | 190 | 10 | 92 |
| 64 | $K_2CO_3$ | 16,200 | 150 | 100 | 35 | 83 |
| 65 | $K_2CO_3$ | 32,400 | 150 | 150 | 15 | 88 |
| 66 | $K_2CO_3$ | 48,500 | 150 | 190 | 10 | 90 |
| 67 | $NaHCO_3$ | 19,700 | 150 | 100 | 35 | 83 |
| 68 | $NaHCO_3$ | 39,400 | 150 | 150 | 15 | 90 |
| 69 | $NaHCO_3$ | 59,500 | 150 | 190 | 10 | 92 |
| 70 | 50% $Na_2CO_3$ 50% $K_2CO_3$ | 14,400 | 150 | 100 | 35 | 84 |
| 71 | 50% $NaCO_3$ 50% $K_2CO_3$ | 28,650 | 150 | 150 | 15 | 89 |
| 72 | 50% $Na_2CO_3$ 50% $K_2CO_3$ | 43,000 | 150 | 190 | 10 | 90 |
| 73 | $CH_3COONa$ | 39,500 | 150 | 150 | 15 | 90 |
| 74 | $(CH_3COO)_3Sb$ | 46,500 | 150 | 150 | 15 | 90 |
| 75 | $(CH_3COO)_2Zn$ | 43,000 | 150 | 190 | 10 | 95 |

What is claimed is:

1. A method of recovering terephthalic acid (TPA) from materials containing poly(ethylene terephthalate) (P.E.T.) through precipitation by acidification with a stronger acid than TPA of an aqueous solution comprising one or more water-soluble metal salts of the TPA and subsequent separation, washing and drying of the precipitated TPA, wherein said solution comprising one or more metal salts of the TPA is obtained by a process comprising the following steps:
   a) mixing, in the absence of water, a reaction mixture comprising said material containing P.E.T. and one or more water-soluble salts of acids weaker than TPA but stronger than water until a water-soluble reaction compound is obtained; said soluble compound being comprised of soluble chemical species obtained following interaction between P.E.T. and said metal salts of weaker acids than the TPA and possible parts of the unreacted P.E.T. or parts of material of different nature than P.E.T., present in the starting material;
   b) adding a fraction of water to the soluble compound obtained from step a), until a reaction of salifying the TPA contained in said soluble chemical species is carried out, so that an aqueous solution is obtained which comprises one or more metal salts of the TPA, ethylene glycol and possible parts of the unreacted starting material.

2. A method of recovering terephthalic acid (TPA) from a material containing poly(ethylene terephthalate) through precipitation by acidification with a stronger acid than the TPA of an aqueous solution comprising one or more metal salts of the TPA and subsequent separation, washing and drying of the precipitated TPA, wherein said solution comprising one or more metal salts of the TPA is obtained by a process comprising the following steps:
   a) mixing, in the absence of water, a reaction mixture comprising said material containing P.E.T. and one or more metal salts of acids weaker than TPA but stronger than water until a water-soluble reaction compound is obtained; said soluble compound being comprised of soluble chemical species obtained following interaction between the P.E.T. and said metal salts of weaker acids than the TPA and possible parts of unreacted P.E.T. or parts of material of different nature than the P.E.T., present in the starting material;
   b) adding a first portion of water to the obtained soluble compound, until a reaction of salifying the TPA contained in said soluble chemical species is achieved but not the complete dissolution of said species, a semi-solid paste being obtained;
   c) eliminating the volatile components present in the semi-solid paste of step b) to obtain a solid residue;
   d) adding a second portion of water to the solid residue obtained from step c), until the TPA is completely solubilized and an aqueous solution comprising one or more metal salts of the TPA is obtained.

3. The method as claimed in claim 1 or 2, wherein the metal salts of weaker acids than the TPA are selected from the group consisting of: sodium carbonate, potassium carbonate, sodium bicarbonate, potassium bicarbonate, sodium sulfide, sodium acetate, potassium acetate, sodium propionate, potassium propionate, sodium benzoate, potassium benzoate, zinc acetate, antimony triacetate, and sodium tetraborate.

4. The method as claimed in claim 3, wherein the metal salt is sodium carbonate.

5. The method as claimed in claim 3, wherein the metal salt is potassium carbonate.

6. The method as claimed in claim 3, wherein the metal salt is sodium sulfide.

7. The method as claimed in claim 3, wherein the metal salt is sodium acetate.

8. The method as claimed in claim 3, wherein the metal salt is sodium bicarbonate.

9. The method as claimed in claim 3, wherein the salt is zinc acetate.

10. The method as claimed in claim 3, wherein the salt is antimony triacetate.

11. The method as claimed in claim 3, wherein the metal salt is present in the form of mixtures of salts.

12. The method as claimed in claim 1 or 2, wherein the reaction mixture of step a) comprises the material containing P.E.T. and a reagent amount sufficient to ensure one to four metal equivalents per mole of terephthalic acid to be salified.

13. The method as claimed in claim 1 or 2, wherein the reaction mixture of step a) further comprises ethylene glycol in an amount by weight between 10:1 and 1:10.

14. The method as claimed in claim 13, wherein the ethylene glycol is added to the reaction mixture at room temperature or pre-heated to a temperature between 100 and 190° C.

15. The method as claimed in claim 1 or 2, wherein the reaction mixture during step a) is mixed, in the absence or in the presence of ethylene glycol, in a propeller reactor at a mixing speed between 600 and 1600 revolutions per minute (r.p.m.), at a temperature between 90 and 260° C. and over a period of time between 5 and 200 minutes.

16. The method as claimed in claim 15, wherein the reaction mixture during step a) is mixed, in the absence or in the presence of ethylene glycol, in a propeller reactor at a mixing speed between 800 and 1500 r.p.m., at a temperature between 95 and 220° C. and over a period of time between 10 and 140 minutes.

17. The method as claimed in claim 1 or 2, wherein in the mixer device the temperature at which formation of the soluble reaction compound takes place, in the absence or in the presence of ethylene glycol, is reached by virtue of a mechanical mixing action alone.

18. The method as claimed in claim 1 or 2, wherein in the mixer device the temperature at which formation of the soluble reaction compound takes place, in the absence or in the presence of ethylene glycol, is reached by virtue of the mechanical mixing action alone and/or by use of heating means.

* * * * *